United States Patent [19]

Van Der Stoel

[11] Patent Number: 4,719,299

[45] Date of Patent: Jan. 12, 1988

[54] PROCESS FOR PREPARING PYRIMIDINE

[75] Inventor: Roland E. Van Der Stoel, Buchten, Netherlands

[73] Assignee: Stamicarbon B. V., Geleen, Netherlands

[21] Appl. No.: 785,998

[22] Filed: Oct. 10, 1985

[30] Foreign Application Priority Data

Oct. 26, 1984 [NL] Netherlands ............... 8403258

[51] Int. Cl.[4] .................................. C07D 239/26
[52] U.S. Cl. ........................................... 544/242
[58] Field of Search ................................ 544/242

[56] References Cited

PUBLICATIONS

Tsuchiya et al., "Syntheses of 2-Alkylpyrimidines by Dehydrogenocyclization of Trimethylenediamine and Aldehydes, and Their Kinetics", (J. Pharmaceut. Soc., Japan), 96, 1005–1012, (1976).
Tsuchiya et al., Synthesis of 2-Alkylpyrimidines by Dehydrocyclization and Dehydrogenation (J. Pharmaceut. Soc., Japan), 97 373–381 (1977).
Tsuchiya et al., CA, vol. 87, 1977, 87:84049e, p. 515.
Tsuchiya et al., CA, vol. 86, 1977, 86:29745h, p. 363.
Okada et al., CA, vol. 84, 1976, 84:17273y, p. 463.
Okada et al., CA, vol. 85, 1976, 85:142251m, pp. 462 and 463.
Okada et al., CA, vol. 90, 1979, 90:549042, p. 608.
Okada et al., "Formation of a 2-Ethylpyrimidine from Frimethylenediamine over Platinum Group Metal-Al$_2$O$_3$ Catalysts and its Kinetic Study", J. Pharmaceut. Soc. Japan, 96, 801–809 (1979) 24 pp.

Primary Examiner—Henry R. Jiles
Assistant Examiner—J. G. Mullins

[57] ABSTRACT

Process for preparing pyrimidine by reacting in the gas phase 1,3-diaminopropane with a $C_1$ reagent in the presence of an excess of methanol and/or carbon monoxide and of a metallic catalyst, wherein the reaction is carried out in the presence of a palladium catalyst promoted with an alkali metal and subsequently from the resulting reaction mixture pyrimidine is recovered.

8 Claims, No Drawings

PROCESS FOR PREPARING PYRIMIDINE

The invention relates to a process for preparing pyrimidine by reacting in the gas phase 1,3-diaminopropane with a $C_1$ reagent in the presence of an excess of methanol and/or carbon monoxide and of a metallic catalyst. Pyrimidine is used, inter alia, as intermediate in the synthesis of organic compounds such as, for instance, crop protection agents.

A process as described in the preamble is known from Yakugaku Zasshi 96: 1005-1012 (1976). This article relates to the gasphase synthesis of 2-alkylpyrimidines from 1,3-diaminopropane and aldehydes in the presence of four catalysts, viz. Pd (2%)—$Al_2O_3$, Pt (2%)—$Al_2O_3$, Rh (2%)—$Al_2O_3$ and Pt (1%)—Rh (1%)—$Al_2O_3$. In the various cyclization experiments the best results were achieved according to this article with the Pt-Rh catalyst and with the Rh catalyst. The Pd catalyst was hardly active. Incidentally the article mentions a pyrimidine yield from 1,3-diaminopropane and formaldehyde of 6% (in addition to 6% 2-methylpyrimidine and 19% 2-ethylpyrimidine). From table I it may be concluded that in this experiment the Pt-Rh catalyst was used. An explanation for the low yield of pyrimidine was sought by the authors at the end of their article in the instability of the proposed intermediate hexahydropyrimidine, as well as in the susceptibility of this intermediate to side reactions. In general the authors advise against the use of Pd catalysts in cyclization reactions as described by them in the said article.

The same research group describes in Yakugaku Zasshi 97: 373-381 (1977) the reaction of 1,3-diaminopropane with methanol to form pyrimidine with a yield of 7%. Details of this reaction are not described, but here again probably the catalyst used was Pt (1%)—Rh (1%)—$Al_2O_3$.

The invention provides a process for preparing pyrimidine in a higher, economically interesting yield. The process according to the invention for preparing pyrimidine by reacting in the gas phase 1,3-diaminopropane with a $C_1$ reagent in the presence of an excess of methanol and/or carbon monoxide and of a metallic catalyst is characterized in that the reaction is carried out in the presence of a palladium catalyst promoted with an alkali metal and subsequently from the resulting reaction mixture pyrimidine is recovered. This makes it possible for a good yield of pyrimidine to be obtained in one reaction step.

$C_1$ reagent is in this connection understood to mean a compound comprising one formyl group (condensable with 1,3-diaminopropane while splitting off water) having the formula HCOX, where X represents a H, OH, $OCH_3$ or $NH_2$ group, as well as carbon monoxide and compounds capable under the reaction conditions of decomposing at least in part to form a compound containing such a formyl group, or to form carbon monoxide.

In the process according to the invention the $C_1$ reagent used may be, for instance, formaldehyde, formamide, methanol, methyl formate, formic acid or carbon monoxide. The $C_1$ reagent applied may, for instance, also be trioxane, which is capable of decomposing under the reaction conditions into formaldehyde, at least in part. Preference is given to the use of methanol, formamide or carbon monoxide as $C_1$ reagent.

The process according to the invention is carried out in the presence of an excess of methanol and/or carbon monoxide. If the $C_1$ reagent used is then at the same time methanol or carbon monoxide, the total reaction system will comprise a minimum of compounds on the supply side. The amount of methanol and/or carbon monoxide is generally 2-100, preferably 5-50, times the amount of 1,3-diaminopropane, calculated on a molar basis. With an amount of methanol and/or carbon dioxide smaller than a twofold molar excess, the yield of pyrimidine will be lower. Amounts larger than a hundredfold excess do not offer any extra advantage, but require a relatively large reactor volume, which has an unfavourable effect on the fixed costs for the preparation of pyrimidine.

As gaseous diluent hydrogen may yet be added to activate the catalyst, as well as to prolong the life of the catalyst, for instance, in a molar ratio of 0-20 calculated in respect of 1,3-diaminopropane.

In the process according to the invention palladium catalysts promoted with alkali metal are used. These catalysts generally contain 0.1-10% (wt) palladium, preferably 0.5-5% (wt), calculated on the total catalyst. The promoter applied may be, for instance, sodium, potassium and lithium, with preference being given to sodium. The amount of alkali metal in the total catalyst may be 0.5-5% (wt), preferably 0.5-2% (wt).

The catalyst can be applied on a support known per se. Such supports may contain, for instance, aluminium oxide, carbon and silicon oxide.

Catalysts as described above are usually commercially available.

The process according to the invention can be carried out at various temperatures, for instance in the range of 200°-550° C. Preference is given to a temperature of 300°-400° C.

For the practical realization of the process according to the invention the modes known per se for realizing gas phase reactions are eligible, for instance the mode of realization in which the gaseous starting mixture is passed over the catalyst in the form of a solid bed or a so-called fluid bed. The space velocity may be varied, for instance between 0.001 and 2 g starting compound per milliliter catalyst material (bulk volume) per hour. The pressure at which the reaction takes place in the gas phase is as such not important, so that the reaction will generally be carried out at autogeneous pressure.

The working up of the pyrimidine obtained in the reaction can take place in a manner known per se by cooling and by subsequently carrying out, for instance, a distillation or extraction.

The invention is further elucidated in the following examples.

EXAMPLE I

Through a vertical tubular reactor, diameter 22 mm and length 400 mm, containing a zone of 50 ml catalyst and provided with a heating jacket, a gaseous mixture of 1,3-diaminopropane, methanol and hydrogen was passed from top to bottom. Per mole, 1,3-diaminopropane 20 moles methanol and 3.5 moles hydrogen were used. The catalyst applied was Pd (1%)—Na (1%) on $\gamma$—$Al_2O_3$. Per ml catalyst 0.12-0.19 g 1,3-diaminopropane was passed through per hour. The temperature of the heating jacket was set at 350° C. Owing to the endothermic reaction that took place in the catalyst bed the temperature in the catalyst bed was a few tens of degrees lower (simultaneous conversion of methanol into carbon monoxide and hydrogen).

The reaction gas was cooled in two steps to 12° C. From the condensed reaction mixture samples were taken at regular time intervals. The composition of the liquid samples was determined gaschromatographically.

On the basis of this determination, as well as of the weight of the 1,3-diaminopropane fed to the reactor and passed over in the relative period of sampling (1 hour), could the conversion of 1,3-diaminopropane and the selectivity to pyrimidine, 2-methylpyrimidine and 2-ethylpyrimidine be calculated.

The selectivity was calculated on converted 1,3-diaminopropane. It was supposed that pyrimidine is formed from an equimolar amount of 1,3-diaminopropane (+methanol). In the calculation of the selectivity for 2-methylpyrimidine and 2-ethylpyrimidine it was assumed that per mole of each of these pyrimidine derivatives 2 moles diaminopropane were required.

For 121 hours a complete conversion of 1,3-diaminopropane was obtained and an average selectivity to pyrimidine of 28%, to 2-methyl-pyrimidine of 2% and to 2-ethylpyrimidine of 8%.

COMPARATIVE EXAMPLE I

In the manner described in example I Pd (1%)—Na (0.06%) on γ-Al$_2$O$_3$ was used as catalyst and 0.25 g 1,3-diaminopropane per ml catalyst was passed through per hour. For six hours a complete conversion of 1,3-diaminopropane was obtained and an average selectivity to pyrimidine of 9%, to 2-methylpyrimidine of 8% and to 2-ethylpyrimidine of 37%.

COMPARATIVE EXAMPLE II

In the manner described in example I Pd (1%)—Na (0.3%)- on γ—Al$_2$O$_3$ was used as catalyst and 0.23 g 1,3-diaminopropane per ml catalyst was passed through per hour. For 2 hours a complete conversion of 1,3-diaminopropane was obtained and an average selectivity to pyrimidine of 10%, to 2-methylpyrimidine of 6% and to 2-ethylpyrimidine of 24%.

EXAMPLE II

In the manner described in example I Pd (1%)—Na (0.8%) on γ—Al$_2$O$_3$ was used as catalyst and 0.13–0.24 g 1,3-diaminopropane per ml catalyst was passed through per hour. For 52 hours a complete conversion of 1,3-diaminopropane was obtained and an average selectivity to pyrimidine of 23%, to 2-methylpyrimidine of 6% and to 2-ethylpyrimidine of 24%.

I claim:

1. Process for preparing pyrimidine by reacting in the gas phase 1,3-diaminopropane with a C$_1$ reagent in the presence of an excess of methanol and/or carbon monoxide and of a metallic catalyst, wherein the reaction is carried out in the presence of a palladium catalyst promoted with from 0.5–2% (wt) alkali metal calculated on the total catalyst, and subsequently recovering pyrimidine from the resulting reaction mixture.

2. Process according to claim 1, wherein the C$_1$ reagent used is formaldehyde, formamide, methanol, methyl formate, formic acid, trioxane or carbon monoxide.

3. Process according to claim 1, wherein the reaction is carried out at a temperature of 300°–400° C.

4. Process according to claim 1, wherein the support used for the catalyst is aluminium oxide.

5. Process according to claim 1, wherein palladium is applied in an amount of 0.5–5% (wt) calculated on the total catalyst.

6. Process according to claim 1, wherein the alkali metal used is sodium.

7. Process according to claim 1, wherein hydrogen is fed to the reaction in a molar ratio of 0–20 in respect of 1,3-diaminopropane.

8. Process according to claim 1, wherein per mole 1,3-diaminopropane 5–50 moles methanol and/or carbon monoxide are used in all.

* * * * *